(12) United States Patent
Budd et al.

(10) Patent No.: US 10,393,667 B2
(45) Date of Patent: Aug. 27, 2019

(54) ANALYSIS USING OPTICAL SENSORS AND SIGNAL ENHANCING AGENTS

(71) Applicant: International Business Machines Corporation, Armonk, NY (US)

(72) Inventors: Russell Budd, North Salem, NY (US); Minhua Lu, Mohegan Lake, NY (US); Vince Siu, Thornhill (CA); Evan Colgan, Montvale, NJ (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/851,288

(22) Filed: Dec. 21, 2017

(65) Prior Publication Data
US 2019/0195808 A1   Jun. 27, 2019

(51) Int. Cl.
*G01N 21/00* (2006.01)
*G01N 21/84* (2006.01)
*G01N 21/78* (2006.01)
*G01N 21/63* (2006.01)
*G01N 21/27* (2006.01)
*G01N 35/00* (2006.01)

(52) U.S. Cl.
CPC ......... *G01N 21/8483* (2013.01); *G01N 21/27* (2013.01); *G01N 21/63* (2013.01); *G01N 21/78* (2013.01); *G01N 2035/00673* (2013.01)

(58) Field of Classification Search
CPC .......... G01T 1/204; G01T 7/02; G01T 1/178; G01T 7/04; G01T 1/203
See application file for complete search history.

(56) References Cited

U.S. PATENT DOCUMENTS

| | | | | |
|---|---|---|---|---|
| 6,096,272 A | * | 8/2000 | Clark | G01N 21/253 422/64 |
| 6,318,191 B1 | * | 11/2001 | Chen | B01F 11/0065 422/68.1 |
| 6,743,597 B1 | | 6/2004 | Guo et al. | |
| 2002/0015149 A1 | * | 2/2002 | Rahbar-Dehghan | B01L 3/5025 356/244 |
| 2005/0129580 A1 | * | 6/2005 | Swinehart | B01F 5/0475 422/400 |
| 2008/0070311 A1 | * | 3/2008 | Li | G01N 15/1459 436/63 |
| 2011/0222062 A1 | * | 9/2011 | Martini | G01N 21/05 356/417 |

(Continued)

*Primary Examiner* — David P Porta
*Assistant Examiner* — Mamadou Faye
(74) *Attorney, Agent, or Firm* — Kristofer Haggerty; Michael J. Chang, LLC

(57) ABSTRACT

Techniques for optical analysis of fluid samples using sensors and water enhancing agents for in-line measurements with a continuous flow of the fluid samples are provided. In one aspect, a device includes: at least one reagent dispenser located at an introduction point along a conduit, the conduit being configured to contain a flow of a fluid sample; at least one first detector located at a first detection point along the conduit downstream from the introduction point; and at least one second detector located at a second detection point along the conduit downstream from the first detection point, wherein the at least one first detector and the at least one second detector are configured to make optical measurements of the fluid sample. A method employing the device is also provided.

4 Claims, 11 Drawing Sheets

(56) References Cited

U.S. PATENT DOCUMENTS

| | | | |
|---|---|---|---|
| 2011/0223673 A1 | 9/2011 | Profitt | |
| 2012/0034702 A1* | 2/2012 | Croud | G01N 21/643 |
| | | | 436/172 |
| 2015/0293021 A1* | 10/2015 | Finkelstein | G01N 21/6452 |
| | | | 506/13 |
| 2017/0370836 A1* | 12/2017 | Gerion | G01N 21/554 |

* cited by examiner

ANALYSIS USING OPTICAL SENSORS AND SIGNAL ENHANCING AGENTS

FIELD OF THE INVENTION

The present invention relates to optical analysis of fluid samples, and more particularly, to techniques for optical analysis of fluid samples using sensors and signal enhancing agents for in-line measurements with a continuous flow of the fluid samples.

BACKGROUND OF THE INVENTION

Diagnostics play a critical role for the detection and prevention of diseases or health-related conditions. Diagnostic tools are used for instance to detect proteins, hormones, pathogens, toxins or metabolites for patients suffering from chronic cardiac diseases, diabetes, infections or allergies, just to name a few. A passive detection scheme is beneficial for routine monitoring as they do not require the patient, doctor or other healthcare provider to actively collect and analyze samples.

Optical analysis is a convenient approach to analyzing fluid samples, where color change is used to signify the presence of various indicators in the sample. However, the reagents typically used for analysis require a particular dwell time for reaction with the sample before the sample can be read. Further, the dwell time varies for different reagents. Thus, employing a passive detection scheme for optical analysis with different reagents is challenging.

Therefore, techniques for optical analysis which enable monitoring a continuous flow of a fluid sample would be desirable.

SUMMARY OF THE INVENTION

The present invention provides techniques for optical analysis of fluid samples using sensors and signal enhancing agents for in-line measurements with a continuous flow of the fluid samples. In one aspect of the invention, a device is provided. The device includes: at least one reagent dispenser located at an introduction point along a conduit, the conduit being configured to contain a flow of a fluid sample; at least one first detector located at a first detection point along the conduit downstream from the introduction point; and at least one second detector located at a second detection point along the conduit downstream from the first detection point, wherein the at least one first detector and at least one second detector are configured to make optical measurements of the fluid sample.

In another aspect of the invention, a method is provided. The method includes: introducing at least one reagent into a fluid sample flowing through a conduit using at least one reagent dispenser located at an introduction point along the conduit; making first optical measurements of an intensity of light $I_1$ passing through the fluid sample at time $t_1$ using at least one first detector located at a first detection point along the conduit downstream from the introduction point; making second optical measurements of an intensity of light $I_2$ passing through the fluid sample at time $t_2$ using at least one second detector located at a second detection point along the conduit downstream from the first detection point; and comparing the first optical measurements with the second optical measurements to determine an amount of reaction, if any, at least one reagent has had with target analyte in the fluid sample between the first detection point and the second detection point.

A more complete understanding of the present invention, as well as further features and advantages of the present invention, will be obtained by reference to the following detailed description and drawings.

DETAILED DESCRIPTION OF PREFERRED EMBODIMENTS

As described above, passively monitoring fluid samples via optical analysis is challenging due to the different dwell times of different reagents used in the analysis. By "passive" it is meant that the monitoring of the sample can be performed without a user (e.g., a patient, doctor, clinician, researcher, etc.) having to actively collect and test the sample. Thus, to use a simple example, if one wanted to monitor particular analytes in a waste water system, passive monitoring would involve analyzing the waste water as it passes through the system. By contrast, active monitoring would require that a user collects a waste water sample from the system and then perform testing on the sample he/she has collected.

Passively monitoring a continuous flow, such as the flow of water in a waste water system, via optical analysis is difficult because one needs to account for the dwell time needed for the reagents to react with their target analytes. If different reagents are used (to detect different target analytes) then it is likely that their dwell times are also different. With conventional approaches, a sample is collected, a reagent(s) is introduced to the sample, and the sample is tested after waiting for the respective dwell time to elapse. However, this approach is not practical in the context of passively monitoring a continuous flow of sample.

Advantageously, provided herein are techniques for making in-line measurements of a continuous fluid flow by taking readings from at least two different points in the flow, and comparing those readings to determine a rate of change of the reaction (between reagent and target analyte). That way, the reactants having different dwell times is not a factor since what is being monitored is the rate of change of the reaction rather than simply a snap-shot of a single point in time. Further, as long as the reaction is still on-going, the start time of the reaction is not important since what is being observed is the change over a given window of time.

To use a simple example to illustrate this concept, say for instance that two reagents (I and II) are introduced to the water flowing through a waste water system, and that reagents I and II target different analytes in the waste water. Further, it is assumed that reagent I and reagent II have different dwell times. For instance, one must wait X seconds after mixing reagent I with the sample containing the target analyte for the reaction to be completed, whereas Y seconds is needed for reagent B, and X Y. However, the reaction begins when the reagents are introduced to the sample. Thus, by looking at the sample between two (fixed) points in the flow (downstream from where the reagents are introduced) one can determine the rate of change of the reaction. Further, it does not matter what stage of the reaction is being observed as long as the reagents are introduced upstream from the observation window and the reaction has not completed or saturated.

Figure 1:
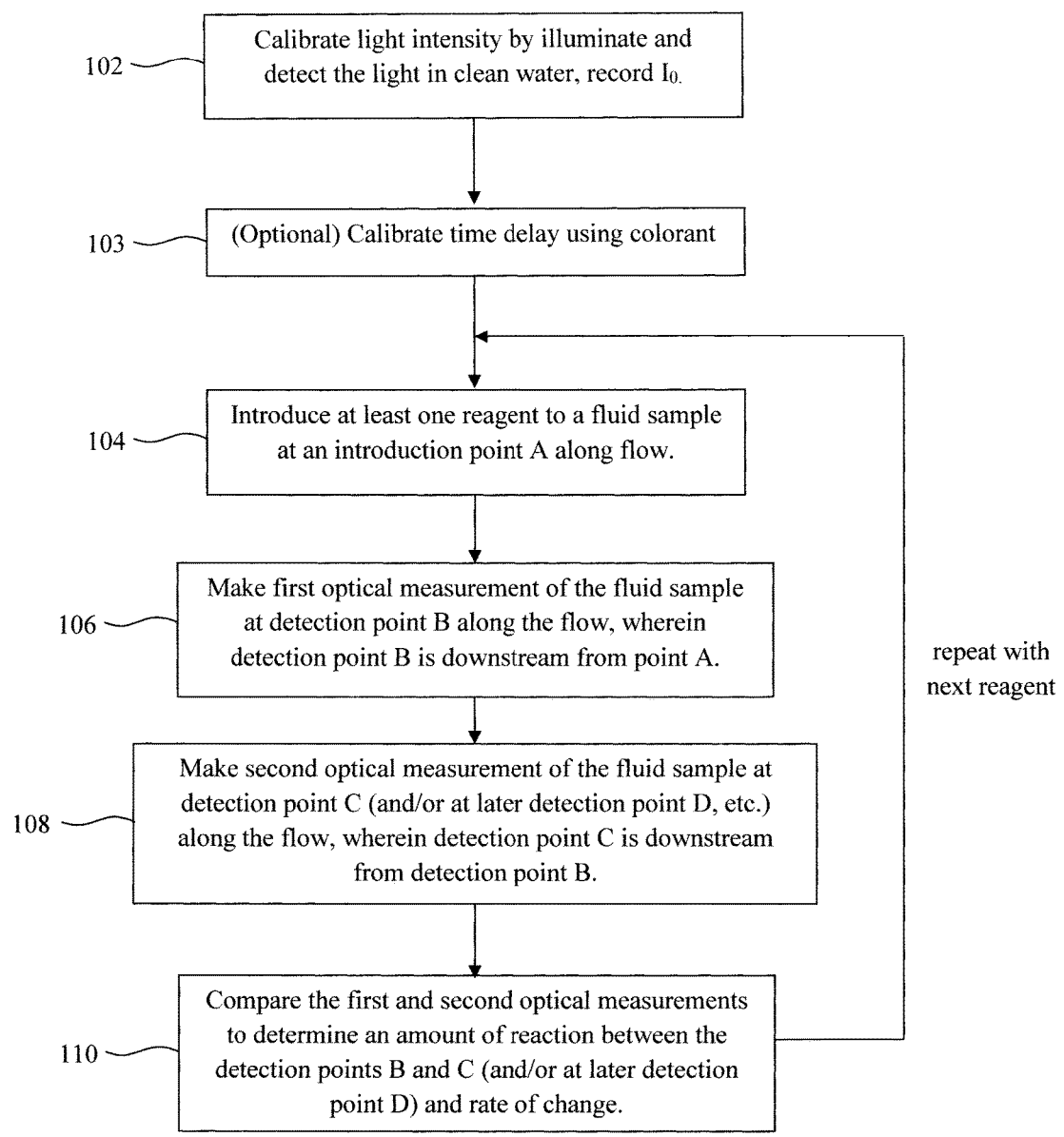
FIG. 1 is a diagram illustrating an exemplary testing method according to an embodiment of the present invention.

An overview of the present techniques is now provided by way of reference to methodology 100 of FIG. 1. As provided above, the present techniques involve making in-line measurements of a continuous flow of a fluid sample. By way of example only, the present techniques can be implemented to monitor waste water systems, and thus can be performed along conduits (e.g., water pipes) leading away from various waste water sources, such as household appliances (including sinks, commodes, etc.). In that case, reagents targeting human biological analytes can be employed to monitor health-related conditions of users.

It is notable however that the present techniques are more broadly applicable to any situation where in-line measurements of a flowing fluid sample would be beneficial. By way of example only, the present techniques can be implemented in drinking water delivery systems to monitor the quality of the water supply. Also, the present techniques can be employed in a manufacturing set-up as a quality control tool for fluid product passing through equipment during production.

In the example that follows, there are at least three different points along the fluid flow that are relevant to the analysis. For clarity, these points will be referred to herein by letters A, B, and C. The first point A is the point at which a reagent(s) is introduced into the fluid sample flow. Thus point A is also referred to herein as introduction point A. The second point B is the point at which a first optical measurement of the flowing fluid sample is made to detect the reagent. Thus point B is also referred to herein as detection point B.

Naturally, the detection point B is located downstream from the introduction point A. The terms 'downstream' and 'upstream' are used throughout the present description to reference points along the fluid sample stream relative to one another. Put simply, the fluid sample flows in a given direction and a first point along the direction of flow before another second point is considered to be upstream from the second point. Conversely, a third point along the direction of flow after the second point is considered to be downstream from the second point.

Further, the fluid sample being analyzed is flowing through a conduit, such as a water pipe, tube, channel, etc. Thus, the introduction and detection points A, B, and C are also used herein to refer to points along the conduit relative to the direction of flow of the fluid sample therethrough. Thus, for example, reagents can be introduced at the introduction point A located along the conduit upstream from the detection points B and C, respectively, which are also located along the conduit.

It is also notable that while the present example involves one introduction point A and two detection points B and C that is merely one exemplary configuration contemplated herein. For instance, multiple introduction points and/or more than two detection points can be implemented in accordance with the present techniques. By way of example only, reagents can be introduced at different points along the flow (rather than having a single introduction point A for all of the reagents). Also, more than two detection points can provide data along a greater length of the flow path allowing for a correspondingly greater reaction time.

As will be described in detail below, the optical measurements of the sample can be made using light sources and light detectors to determine the transmission intensity (I) of light through the sample (with reagent). Suitable light sources include, but are not limited to, light emitting diodes (LEDs) with various wavelengths, a laser, arc lamps, halogen lamps and/or an incandescent lamp, and suitable light detectors include, but are not limited to, a spectrometer, photodiodes (PD), a charge-coupled device/complementary metal oxide semiconductor CCD/CMOS imager, and/or photomultiplier tubes. Further, color filters can be used so that different light detectors respond to different wavelengths of light or an illumination system can be employed that sequentially provides different wavelengths of light at different times using, e.g., a sequence of LEDs or lights in combination with filters.

As will be described in detail below, the data extracted from the detection points B and C is calibrated using baseline intensity $I_{0i}$ readings taken without any signal enhancements or colorants in the water. Thus, prior to introducing a sample, readings are taken of clean water in the conduit using the light source/detector pairs at detection points B and C, and those readings recorded as $I_{0i}$. As will also be described in detail below, data extracted from the detection points B and C will be used to determine the rate of change of the reaction based on the time delay between the two detection points B and C, i.e., the time that elapses between when the fluid sample passes the detection point B and when it passes detection point C. Thus, according to an exemplary embodiment, the system is also calibrated to determine the time delay between the detection points B and C. Namely, in step 103 a colorant (e.g., a dye, stain or other visible detector) is added to the fluid sample flow (at introduction point A), and the time is measured between when the colorant is detected at the first detection point B (i.e., time $t_1$) and when the colorant is detected at the second detection point C (i.e., time $t_2$).

Calibrating the time delay using a colorant (step 103) is, however, optional. The "center max" of the color change from the reagent can instead be used to determine the time delay. For instance, when measuring a sample/reagent the light detectors take readings continuously. The time $t_1$ and $t_2$ can simply be determined by the time at which the intensity measurement is at its minimum or maximum at detection points B and C, respectively.

With regard to calibration, these same light sources and detectors can be used to determine the time $t_1$ when the colorant is detected at the detection point B and the time $t_2$ when the colorant is detected at the detection point C. The time delay, i.e., $t_2-t_1$, between the detection points B and C will later be used in calculating the rate of change of the reactants during testing.

In step 104, at least one reagent is introduced to the fluid sample flow. As provided above, the regents are introduced at an introduction point A which is upstream from the detection points B and C. As will be described in detail below, the reagents can be contained in reservoirs connected by valves to the conduit through which the fluid sample is flowing. The valve can be manually operated or automated (computer-controlled) to dispense a given amount of reagent from a given reservoir in a given sequence. For example, in accordance with one exemplary embodiment, a first given reagent is dispensed into the fluid sample flow and measured, followed by a second reagent being dispensed into the fluid sample flow and measured, and so on. Thus, in that case, the reagents need to be dispensed in the correct sequence and at the right time (i.e., so as to have only one reagent being measured at a time). This coordination can be achieved via the valve(s) and separate reservoirs for the reagents. By way of example only, suitable computer-controllable micro-miniature solenoid valves for dispensing fluids are commercially-available from ASCO, Florham Park, N.J.

As highlighted above, the reagents react with target analytes in the sample, changing the color of the sample which is detected via the optical measurements made at the detection points B and C. In order to obtain measurements with a uniform concentration of the reagents, according to an exemplary embodiment the reagent is introduced in step 104 for a sufficient amount of time to enable a uniform concentration of the regent to be detected at the detection points B and C (see steps 106 and 108—described below). Namely, when the reagent is dispensed into the fluid flow, the regent 'slug' will broaden as it travels along the direction of flow. Thus, a concentration of the reagent at the front and back of the slug will be less than at the center. However, by dispensing the reagent over a sufficient duration will enable a constant concentration of the reagent at the center of the slug for detection. This concept is further illustrated by way of reference to FIG. 2, below.

As highlighted above, the present techniques can be implemented for analyzing human biological analytes, e.g., to monitor health-related conditions of users. According to an exemplary embodiment, the present techniques are performed for urinalysis on wastewater from a commode. By way of example only, urinalysis can target the detection of certain biomarkers such as pH, specific gravity, leucocytes, nitrate, protein, glucose, ketones, urobilinogen, bilirubin, and blood, and may also include other biomarkers for sepsis/inflammation, bacterial speciation, tumor markers, and fibril aggregation.

In step 106, first optical measurements are made of the fluid sample at the detection point B, wherein the intensity of light of one or more colors, or bands of different wavelengths, passed through the fluid sample at the detection point B (i.e., $I_1$) is measured. As described above, detection point B is downstream from the point A where the reagents are introduced into the fluid sample flow.

In step 108, second optical measurements are made of the fluid sample at the detection point C, wherein the intensity of light of one or more colors, or bands of different wavelengths, passed through the fluid sample at the detection point C (i.e., $I_2$) is measured. As described above, detection point C is downstream from both the introduction point A and the detection point B.

In step 110, the intensity $I_1$ from the first optical measurement at detection point B (step 106) and the intensity 12 from the second optical measurement at detection point C are compared along with the delay time between the detection points B and C (see above) to determine the rate of change as:

$$(I_2/I_{02}-I_1/I_{01})/(t_2-t_1), \quad (1)$$

wherein $I_{0i}$ is the intensity of the light at specific wavelength/color without colorant in clean water (see calibration step 102).

As shown in FIG. 1, the process can then be repeated with one or more additional reagents in the same manner described. This enables the detection of multiple analytes in the fluid sample flow via various different reagents.

Notably, it does not matter what stage of the reaction is being observed as long as the reagents are introduced upstream from the observation window and the reaction has not completed or saturated. This concept is illustrated by way of experimental data provided in FIG. 10—described below.

Figure 2:
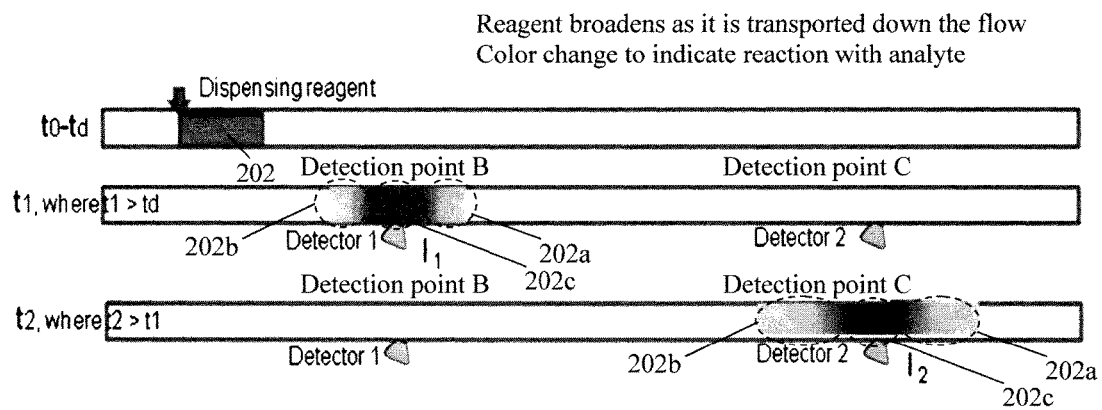
FIG. 2 is a schematic diagram illustrating a reagent at different points along the flow of a fluid sample according to an embodiment of the present invention.

As provided above, the reagent is preferably introduced in step 104 for a sufficient amount of time to enable a uniform concentration of the regent to be detected at the detection points B and C (see steps 106 and 108—described below). See, for example, FIG. 2. As shown in FIG. 2, at the time $t_d$ when it is dispensed (at time $t_0$), the reagent forms a 'slug' 202 of the reagent molecules in the fluid sample flow. As the reagent slug 202 is transported along with the fluid sample, the reagent will broaden out such that by the time ($t_1$) the regent reaches a first detector (detector 1) at the detection point B front and back regions (202a and 202b) of the slug 202 will have become diffuse. Lighter shading is used in these regions to indicate that they contain a lower concentration of the reagent (e.g., than the center region 202c of the slug 202). However, if the reagent is dispensed for a long enough duration—relative to the flow rate of the fluid sample), then the center region 202c of the slug will contain a constant concentration of the reagent (preferably at the as-dispensed concentration). Although turbulent flow without air bubbles can work, the flow prefers to be laminar flow for better accuracy, and the length of the "slug" need to be long enough so that at time $t_2$ the center of the slug has not yet been diluted. Low velocity is needed for laminar flow. Flow is laminar when the Reynolds number is below a critical value. The Reynolds number depends on the geometry of the conduit, viscosity of the liquid and flow rate. The reagent concentration profile will further broaden by the time ($t_2$) the reagent reaches a second detector (detector 2) at the detection point C. See FIG. 2 where the front and back regions 202a and 202b of the slug have increased in area. However, the center region 202c still contains a constant concentration of the reagent.

As shown in FIG. 2, intensity measurements $I_1$ and $I_2$ are taken, via Detector 1 and Detector 2 at the detection points B and C, respectively. The maximum, or minimum, values of $I_1$ and $I_2$ at these detection points B and C will represent readings taken from the center region 202c of the slug 202. The time of detection of the maximum/minimum in light intensity $I_1$ and $I_2$ is denoted as $t_1$ and $t_2$ for the rate of the change calculation.

Figure 3:
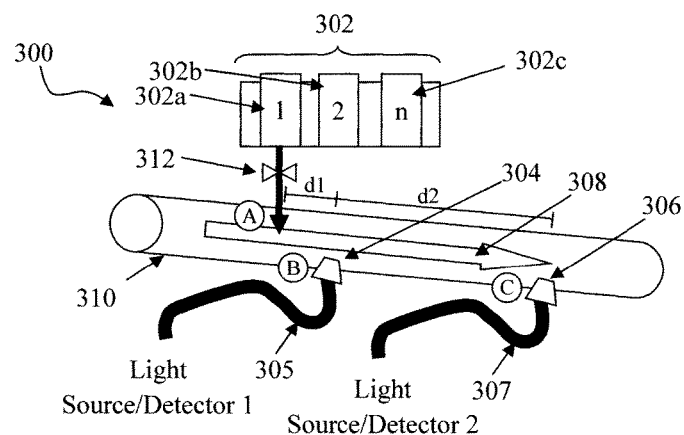
FIG. 3 is a diagram illustrating an exemplary diagnostic device including a reagent dispenser, a first optical window connected to a first light source and detector and a second optical window connected to a second light source and detector along a conduit according to an embodiment of the present invention.

An exemplary diagnostic device 300 for performing methodology 100 of FIG. 1 is shown in FIG. 3. As shown in FIG. 3, diagnostic device 300 includes at least one reagent dispenser 302, at least one (first) optical window 304, and at least one (second) optical window 306. An arrow 308 is used to indicate the direction of flow of fluid sample through a conduit 310.

The reagent dispenser 302 is located along the conduit 310 at introduction point A upstream from the optical windows 304 and 306. The reagent dispenser 302 includes at least one reagent reservoir 302a, 302b, 302c, etc. each containing at least one reagent (reagent 1, reagent 2, . . . , reagent n, respectively). A valve 312 connecting the reagent dispenser 302 to the conduit 310 controls how much of the reagent from each of the respective reservoir 302a, 302b, 302c, etc. is dispensed into the conduit 310 at introduction point A and when. As provided above, the valve 312 can be manually operated (e.g., a user opens the valve for a desired duration) or can be computer-controlled. It is notable that valve 312 is representative of one or more of the valves that may be used to dispense the reagents from the reservoirs. For instance, embodiments are contemplated herein where there is one valve 312 for each of the reservoirs. In that case, a single valve 312 controls its respective reservoir. One valve 312 can instead be used to dispense from all of the reservoirs. In that case, it might be advantageous to include an intervening cleaning step between reagents to clean the valve. For instance, instead of a reagent, every other reservoir can contain water or other suitable cleaning solution. Thus, when dispensing the contents of the reservoirs in series, the valve will dispense reagent, then cleaning solution, and so on.

As also provided above, the valve 312 performs several functions. One important function performed by valve 312 is to dispense the reagents in the proper sequence. Namely, as provided above, a first reagent can be dispensed into the fluid sample flow and then tested, followed by a second reagent which is dispensed into the fluid sample and tested, and so on. This action is regulated by the valve 312 by opening each of the reagent reservoirs 302a, 302b, 302c, etc. in turn, at the proper times. Another important function performed by valve 312 is controlling the amount of time the reagent is dispensed into the fluid sample flow. Namely, as provided above, the reagent slug dispensed at the introduction point A broadens out as it travels along the fluid flow. However, depending on the rate of fluid flow, if the reagent is dispensed for a long enough duration then a region will remain at the center of the slug having a uniform concentration for testing. The amount of time (i.e., duration) the reagent is dispensed into the conduit 310 is regulated via the valve 312.

The optical windows 304 and 306 provide (optical) access into the conduit 310. As shown in FIG. 3, optical window 304 is located along the conduit 310 at a detection point B and optical window 306 is located along the conduit 310 at a detection point C. Detection points B and C are both downstream from the introduction point A (at which the reagent dispenser 302 is located). Further, detection point C is located downstream from detection point B. Thus, given the direction of flow 308, measurements of the fluid sample can be made at detection point B at a first time $t_1$, and measurements of the fluid sample can be made at detection point C at a second (later) time $t_2$, wherein $t_2 > t_1$. As provided above, based on the measurements made at time $t_2$ and time $t_1$, and the (previously determined) delay time between the detection points, a rate of change can be calculated. See Equation 1, above.

In the exemplary embodiment shown in FIG. 3, the optical window 304 and the optical window 306 are connected via optical waveguides 305 and 307 to a first light source and detector (Light source/Detector 1) and a second light source and detector (Light source/Detector 2), respectively. A variety of light source and light detector configurations are contemplated herein (see below). In general however, the windows 304 and 306 permit light to be passed through the conduit 310 enabling optical data to be extracted from the fluid sample. The light is delivered to/from the conduit 310 from/to the light sources and light detectors via the optical waveguides 305 and 307. Optical waveguides include, but are not limited to, optical fibers and rectangular waveguide. The light sources can have multiple colors or a broad spectrum. Preferably, the light detectors can take light intensity measurement or spectrum (light intensity at a range of wavelengths) measurement.

Figure 4:
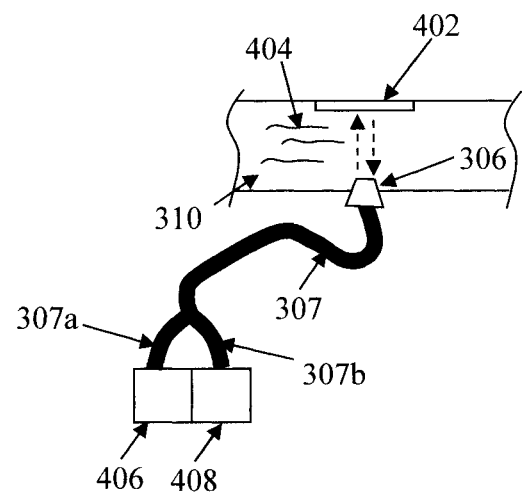
FIG. 4 is a diagram illustrating an exemplary light source and detector configuration for reflective measurements according to an embodiment of the present invention.

One light source and light detector configuration contemplated herein involves reflective measurements. See FIG. 4. For illustrative purposes only, FIG. 4 depicts a section of conduit 310 having the optical window 306. In this particular example, the optical window 306 is present on a first side of the conduit 310 and a reflective surface 402 is present on a second side of the conduit opposite the optical window 306. That way, light introduced into the conduit through the optical window 306 will pass through the fluid sample 404, and then be reflected back through the sample again to the optical window 306 via the reflective surface 402. This configuration measures the transmittance of the sample with the path length in the sample being two times that of the distance between the optical window 306 and the reflective surface. According to an exemplary embodiment, the reflective surface 402 is a mirror mounted to the second side of the conduit opposite the optical window 306. By way of example only, a mirror can be mounted inside the conduit 310 using an adhesive. Alternatively, according to another exemplary embodiment, the reflective surface 402 is a polished surface along the second side of the conduit opposite the optical window 306. Polishing the surface of, e.g., a metal, conduit 310 will increase its light reflectivity properties essentially acting as a mirror would in reflecting light back to the optical window 306. Alternatively, an additional optical window can be provided into the conduit and the reflective surface (e.g., a mirror) can be mounted outside of the conduit.

As shown in FIG. 4, a light source 406 and a light detector 408 are coupled to the optical window 306 via optical waveguide bundles 307. As provided above, suitable light sources include, but are not limited to, light emitting diodes (LEDs), and/or laser, arc lamp, halogen lamp, incandescent lamp, and suitable light detectors include, but are not limited to, a spectrometer, photodiodes (PD), charge-coupled device/complementary metal oxide semiconductor CCD/CMOS imagers, and/or a photomultiplier tube. As shown in FIG. 4, the light source 406 and light detector 408 are coupled through separate optical fibers/waveguides 307*a* and 307*b*, respectively, to the optical window 306. As also shown in FIG. 4, the optical fibers/waveguides 307*a* and 307*b* can be combined into a single bundle 307 for coupling to the optical window 306. Suitable optical fiber/waveguide bundles are commercially available, for example, from Thorlabs, Inc., Newton, N.J., whereby the sample end will be attached to the optical window 306 and the other two ends are connected to light source 406 and light detector 408.

Figure 5:
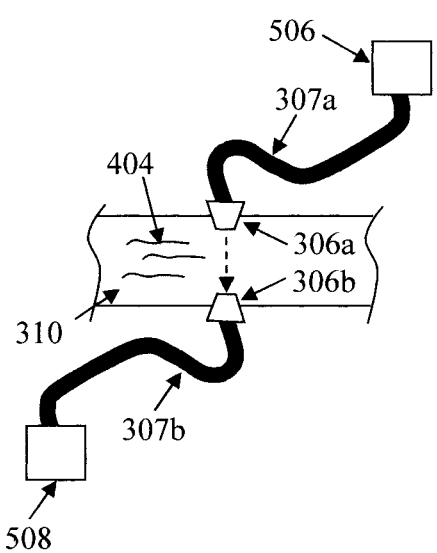
FIG. 5 is a diagram illustrating an exemplary light source and detector configuration for transmissive measurements according to an embodiment of the present invention.

Another light source and light detector configuration contemplated herein involves direct transmissive measurements. See FIG. 5. For illustrative purposes only, FIG. 5 depicts a section of conduit 310 having two optical windows 306*a* and 306*b*. In this particular example, the optical window 306*a* is present on a first side of the conduit 310 and the optical window 306*b* is present on a second side of the conduit 310 opposite the optical window 306*a*. That way, light introduced into the conduit through the optical window 306*a* will pass through the fluid sample 404 and then be picked up by the optical window 306*b*. The path length in the sample is the distance between the optical windows 306*a* and 306*b*. A notable difference between the set-up in FIG. 5 (direct transmissive measurements) versus that in FIG. 4 (reflective measurements) is the path length. In some applications, shorter path length detection might be preferable. For instance, if the sample is very absorbing, the longer path length might reach the detection limit of the detector. In that case, a shorter path length might help extend the detection range. Also, the reflective surface (e.g., mirror) might not be achromatic. A direct transmission measurement can eliminate the variation introduced by the reflective surface.

In this exemplary embodiment, the optical window 306*a* is coupled to a light source 506 via an optical waveguide 307*a*, and the optical window 306*b* is coupled to a light detector 508 via an optical waveguide 307*b*. As such, light produced by the light source will travel along the optical waveguide 307*a* to the optical window 306*a* where it enters the conduit 310. The light passes through (i.e., transmissive) the fluid sample 404 and is picked up on the opposite side of the conduit 310 by the optical window 306*b*. The light entering the optical window 306*b* will travel along the optical waveguide 307*b* to the light detector 508.

It may be desirable to vary the time between when the reagent is dispensed into the fluid sample flow at time $t_d$ and when measurements are made along the direction of flow at time $t_1$ and/or when measurements are made along the direction of flow at time $t_2$. Doing so will increase/decrease the reaction time between the reagents and the target analyte in the fluid sample. Varying the reaction time can be useful, for example when the fluid flow rate is high, to allow more time between when the reagent is introduced and when measurements are made.

Figure 6:
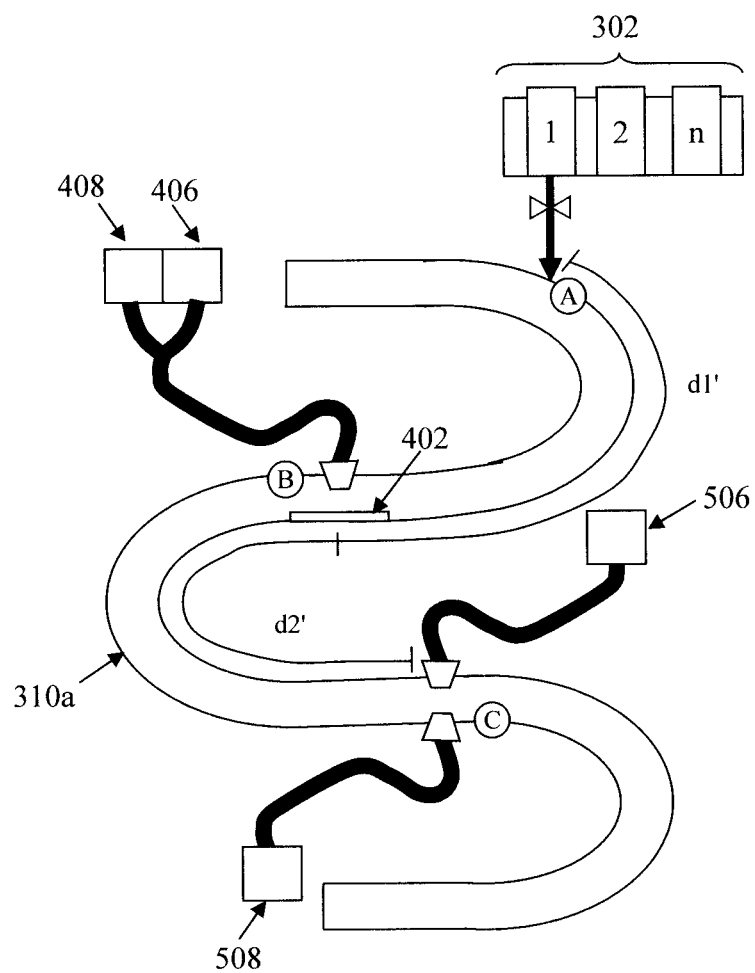
FIG. 6 is a diagram illustrating an exemplary configuration of the present diagnostic device having a conduit with a serpentine shape according to an embodiment of the present invention.

According to one exemplary embodiment, the reaction time is varied by physically varying the location of the introduction point A and the detection point B and/or between the detection point B and the detection point C. For instance, as shown in FIG. 6, a variation of the conduit 310*a* is employed having a meandering or serpentine configuration. Doing so increases the distance between the introduction point A and the detection point B and between the detection point B and the detection point C. For instance, comparing FIG. 6 with FIG. 3, it can be seen that employing a straight conduit 310 (FIG. 3) a distance d1 is present between the introduction point A and the detection point B, and a distance d2 is present between the detection point B and the detection point C. However, with the serpentine configuration in conduit 310*a* shown in FIG. 6, a longer distance is d1' is now present between the introduction point A and the detection point B (i.e., d1'>d1), and a longer distance d2' is now present between the detection point B and the detection point C (i.e., d2'>d2). Of course, these distances can be tailored accordingly depending on the placement of the reagent dispenser (at introduction point A) and the optical windows (at detection points B and C) along the conduit.

FIG. 6 also illustrates how the different reflective (FIG. 4) and transmissive (FIG. 5) device configurations can be incorporated into the overall design. While both modes of detection can be incorporated into the same detection system (as shown in FIG. 6), this is not a requirement. In fact, for ease of implementation it may be preferable to employ a single type (reflective or transmissive) of detector throughout the system. That way, any time a detector needs to be replaced it can easily be swapped out with another detector of the same design.

Another factor affecting reaction time is the flow rate of the fluid sample flow through the conduit. Namely, the flow rate affects how quickly the reagents dispensed at the introduction point A (and which are transported with the sample flow) reach the detection points B and C. Thus, regulating the flow rate will enable control of the reaction time. Embodiments are also contemplated herein where a mechanism is employed to control the flow rate of the fluid sample through the conduit 310. See, for example, FIG. 7.

Figure 7:
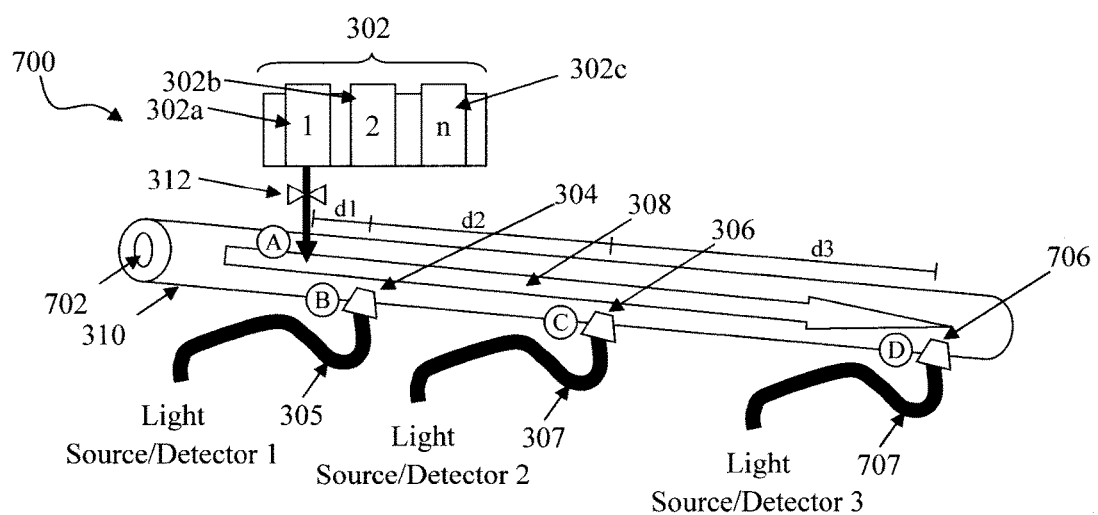
FIG. 7 is a diagram illustrating an exemplary configuration of the present diagnostic device having more than two detection points according to an embodiment of the present invention.

FIG. 7 illustrates an exemplary diagnostic device 700. Diagnostic device 700 represents a variant of the diagnostic device 300 shown in FIG. 3 and as such like structures are numbered alike in both figures. As shown in FIG. 7, a restricted orifice 702 is employed at the entrance to conduit 310 upstream from the introduction and detection points A, B, C, etc. The restricted orifice 702 reduces the size of the opening through which the fluid sample enters the conduit 310 and thereby reduces the flow rate of the fluid sample through the conduit. While the restricted orifice 702 is shown disposed at the entrance to the conduit, it is to be understood that this flow-restriction mechanism can be employed at any point(s) in the conduit 310 along the direction of flow, including but not limited to, between the introduction point A and the detection point B and/or between the detection point B and the detection point C, etc.

Further, as provided above the use of two detection points B and C is merely an example, and in fact the device can include more than two detection points. For instance, as shown in FIG. 7 a third detection point D is employed downstream from detection point C. The detection point D can be configured in any manner described above. For example, the detection point D shown in FIG. 7 includes an optical window 706 located in the conduit 310 (downstream from detection point C) that is connected via optical waveguide 707 to a third light source and detector (Light source/Detector 3). By way of example only, the detection point D can be configured to take reflective measurements, and thus would be configured as described for example in conjunction with the description of FIG. 4 above to include a light source and a light detector coupled to an optical window and a reflective surface present opposite the optical window. Alternatively, the detector point D can be configured to take direct transmissive measurements, and thus would be configured as described for example in conjunction with the description of FIG. 5 above to include a light source and a light detector coupled to optical windows on opposite sides of the conduit. As also shown in FIG. 7, a distance d1 separates the introduction point A from the detection point B, and a distance d2 separates the detection point B from detection point C. Detection point D can be located that same distance (d2) downstream from the detection point C. However, a uniform spacing between the detection points B, C and D is not required. In fact, as shown in FIG. 7 the detection point D is located a distance d3 away from the detection point C, wherein $d3 \neq d2$. In the particular example shown $d3 > d2$. However, embodiments are contemplated herein where $d3 < d2$.

With more than two detection points the range of detection can be increased. For instance, by way of reference to methodology 100 of FIG. 1, in step 108 optical measurements can be made at both detection point C and detection point D, and in step 110 those readings are compared with the measurements made at detection point B. That way, a greater range of values can be gleaned from the sample. For instance, since detection point D is farther away from detection point B, a greater change of signal intensity between B→D may be detected than from B→C.

Figure 8:
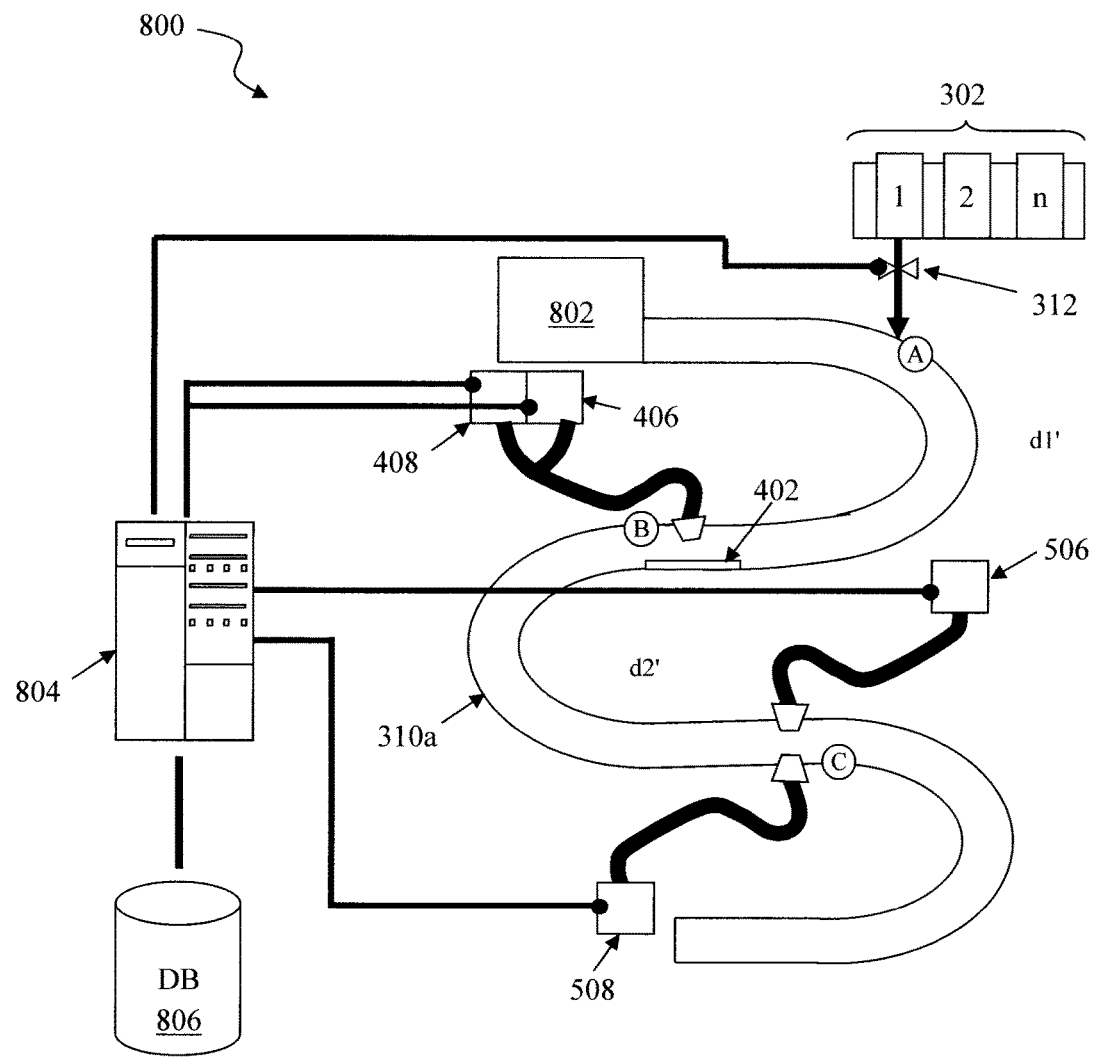
FIG. 8 is a diagram illustrating an exemplary detection system according to an embodiment of the present invention.

FIG. 8 is a diagram illustrating an exemplary detection system 800. Detection system 800 can employ any of the configurations described above. For illustrative purposes only, system 800 is shown to include the serpentine conduit configuration described in conjunction with the description of FIG. 6 above, and like structures are numbered alike in FIG. 8.

As shown in FIG. 8, the conduit 310a leads away from a sample collector 802, such as a household appliance (e.g., sinks, commodes, etc.). Thus, detection system 800 is configured to analyze the continuous flow of a fluid sample from the sample collector 802. Sample collector 802 can also include a storage sub-unit that is connected to, but isolated from, the main source so that a fluid sample can be stored for sub-sequential measurement, while the appliance is used. Having such a storage sub-unit is preferable since the detection might take more time than a person wants to wait to use the appliance. An exemplary conduit having a storage sub-unit and method for use thereof is described in conjunction with the description of FIGS. 11 and 12, below. Sample collector 802 and the conduit 310 can be cleaned between uses, and clean water will be refilled.

Detection system 800 includes a computer device 804 that is configured to control and extract data from the various diagnostic devices. For instance, as shown in FIG. 8, computer device 804 is in communication with each light source 406/506 and a light detector 408/508 in the system. Computer device 804 controls when each of the light sources 406/506 is turned on, and in turn collects the intensity (I) data extracted from the fluid sample via the light detector 408/508. Data collected from the light detector 408/508 by the computer device 804 is stored in a database (DB) 806.

According to an exemplary embodiment, computer device 804 also controls when and how much of each reagent is dispensed. For instance, as shown in FIG. 8 computer device 804 can control the valve 312 that regulates the dispensing of the reagents from the reagent dispenser 302. In that case, the computer device 804 can coordinate the data collection with the reagent it is currently having dispensed.

Figure 9:
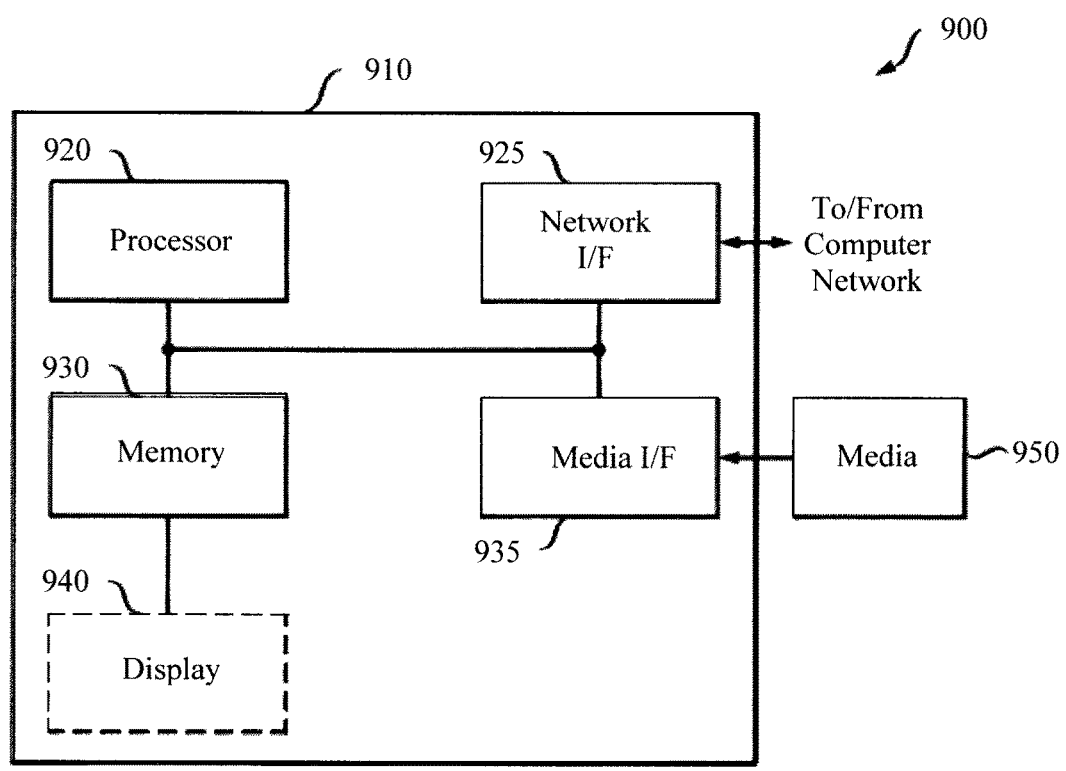
FIG. 9 is a diagram illustrating an exemplary apparatus that can be configured to implement one or more of the methodologies presented herein according to an embodiment of the present invention.

Turning now to FIG. 9, a block diagram is shown of an apparatus 900 that can be configured to perform one or more of the methodologies presented herein. For example, apparatus 900 can serve as the computer device 804 in system 800 of FIG. 8 and can be configured to perform one or more of the steps of methodology 100 (of FIG. 1) described above. Apparatus 900 includes a computer system 910 and removable media 950. Computer system 910 includes a processor device 920, a network interface 925, a memory 930, a media interface 935 and an optional display 940. Network interface 925 allows computer system 910 to connect to a network, while media interface 935 allows computer system 910 to interact with media, such as a hard drive or removable media 950.

Processor device 920 can be configured to implement the methods, steps, and functions disclosed herein. The memory 930 could be distributed or local and the processor device 920 could be distributed or singular. The memory 930 could be implemented as an electrical, magnetic or optical memory, or any combination of these or other types of storage devices. Moreover, the term "memory" should be construed broadly enough to encompass any information able to be read from, or written to, an address in the addressable space accessed by processor device 920. With this definition, information on a network, accessible through network interface 925, is still within memory 930 because the processor device 920 can retrieve the information from the network. It should be noted that each distributed processor that makes up processor device 920 generally contains its own addressable memory space. It should also be noted that some or all of computer system 910 can be incorporated into an application-specific or general-use integrated circuit.

Optional display 940 is any type of display suitable for interacting with a human user of apparatus 900. Generally, display 940 is a computer monitor or other similar display.

Figure 10:
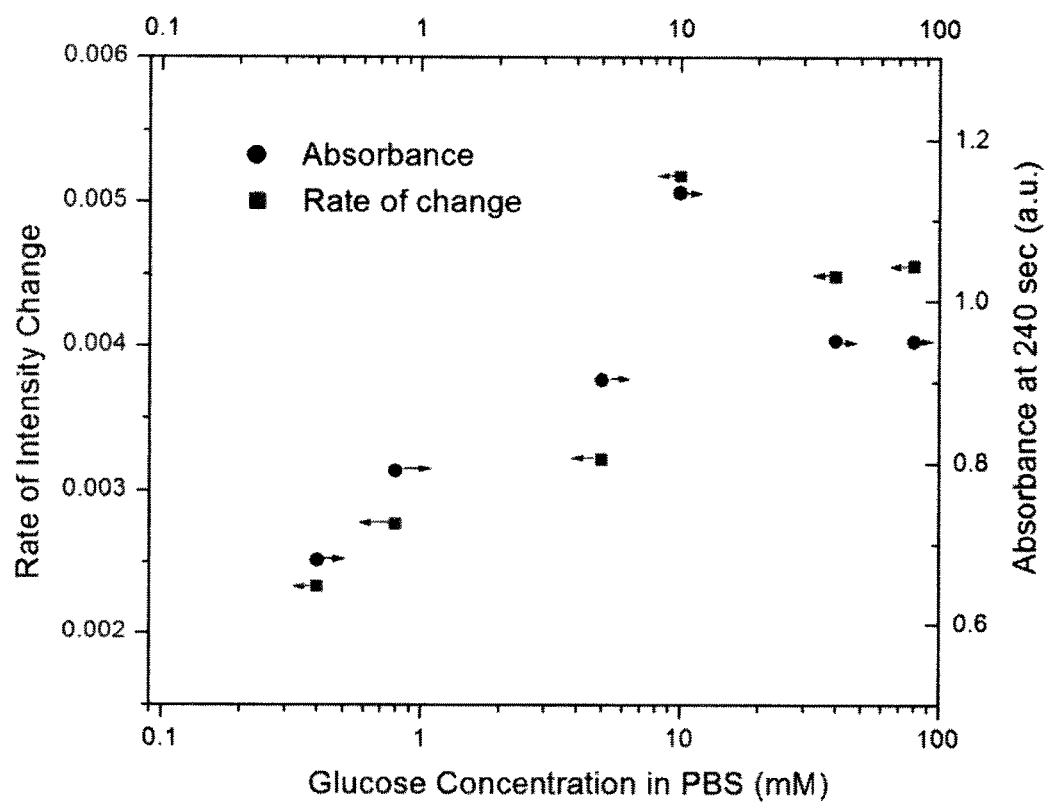
FIG. 10 is a diagram illustrating experimental data comparing the absorbance/transmittance measurement and the rate of the change in absorbance/transmittance measurement for a reagent according to an embodiment of the present invention.

FIG. 10 is a diagram of experimental data (for glucose as a target analyte) that compares absorbance/transmittance measurement to the rate of change in the absorbance/transmittance measurement. As shown in FIG. 10, the rate of change measurement has a monotonic correlation to the concentration of the analyte as the absorbance measurement. However, for some reactions that take up to 30-60 second to complete, the rate of the change measurement of faster and less sensitive to the time of the measurement. It is notable that for very fast reactions, that the reaction completes before reaching to point B or C, transmittance or absorbance can also be used as a parameter of the measurement.

Figure 11:
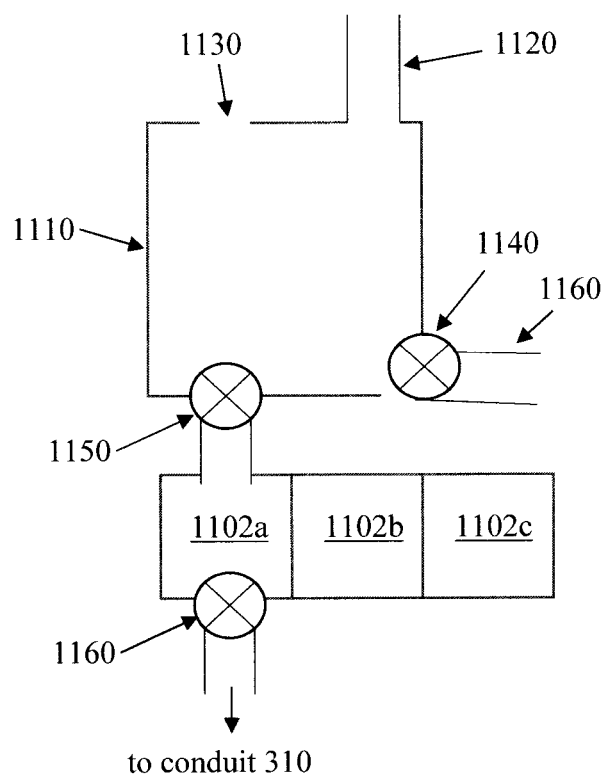
FIG. 11 is a diagram illustrating an exemplary sample collector having a storage sub-unit according to an embodiment of the present invention.
Figure 12:
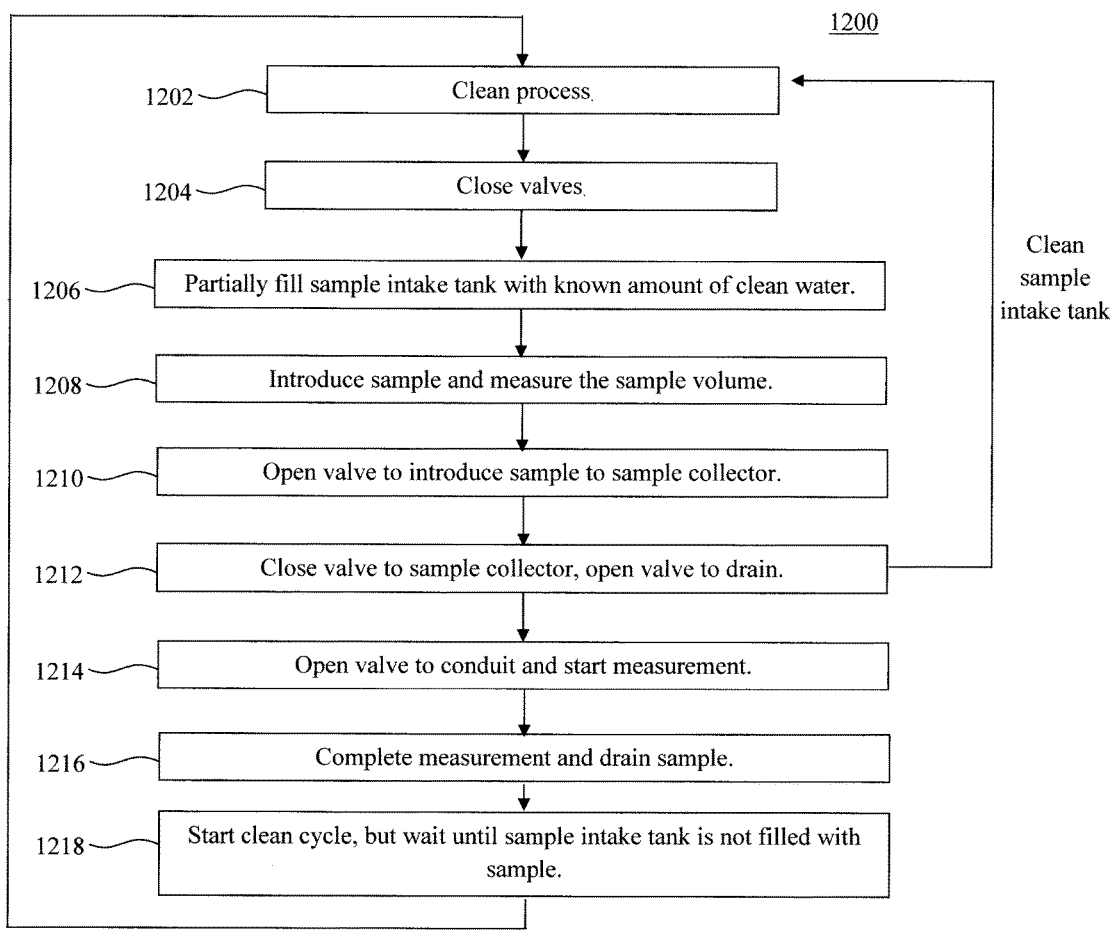
FIG. 12 is a diagram illustrating an exemplary methodology for using the exemplary sample collector of FIG. 11 according to an embodiment of the present invention.

As provided above, the present detection system can include a sample collector having a storage sub-unit that is connected to, but isolated from, the main source so that a fluid sample can be stored for sub-sequential measurement. An exemplary sample collector 1100 having a storage sub-unit is now described by way of reference to FIG. 11. FIG. 11 will be described along with FIG. 12 which depicts an exemplary methodology 1200 for use of sample collector 1100.

FIG. 11 is a diagram illustrating an exemplary sample collector apparatus 1100. As shown in FIG. 11, sample collector apparatus 1100 includes a main sample intake tank 1110 that has a clean water port 1120 that connects to a clean water supply and is programmed to flush clean the sample intake tank 1110 and sample collector 1102a,b,c, and conduit 310. A cleaning process is first performed (see step 1202) whereby clean water is introduced into sample intake tank 1110 to clean the sample intake tank 1110, and the waste water removed via drain 1160. Clean water can also be introduced into sample collector 1102a,b,c, and to conduit 310 through valves 1150 and 1160 to clean the sample collector and conduit after analysis. After the cleaning process, and the waste water has been drained, the valves are closed (see step 1204).

A known amount of clean water is introduced into the sample intake tank 1110 to partially fill the tank (see step 1206). The sample deposits into the sample intake tank 1110 through sample entry port 1130. The amount of the sample deposition can be measured (see step 1208). With reference to the known amount clean water in the sample intake tank 1110, a sample dilution factor can be calculated. The sample in sample intake tank 1110 can then be introduced into one of the sample collector 1102*a,b,c* through valve 1150 (see step 1210). The unused sample in sample intake tank 1110 will be drained through valve 1140 (see step 1212). Valve 1160 introduces the sample into conduit 310 when measurement starts (see step 1214). The sample intake tank 1110 will be flushed and cleaned with clean water and drained through valve 1140 (see step 1216). Optionally, cleaning agents (not shown) can also be introduced into sample intake tank 1110 during the cleaning cycle. The sample intake tank 1110 will be partially filled with known amount of clean water and the system is ready for the next sample. After the completion of the analysis, the sample collector 1102*a,b,c*, valves 1140, 1150 and 1160, and conduit 310 will be cleaned by clean water and optional cleaning agents (see step 1218). This cleaning step waits until the sample intake tank 1110 is not loaded with sample.

Figure 13A:
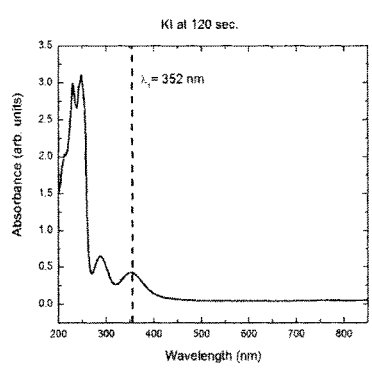
FIG. 13A is a diagram illustrating experimental data of optical measurement of glucose (analyte) using KI as a reagent according to an embodiment of the present invention.
Figure 13B:
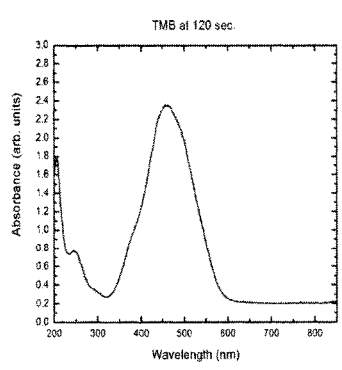
FIG. 13B is a diagram illustrating experimental data of optical measurement of glucose (analyte) using TMB as a reagent according to an embodiment of the present invention.
Figure 13C:
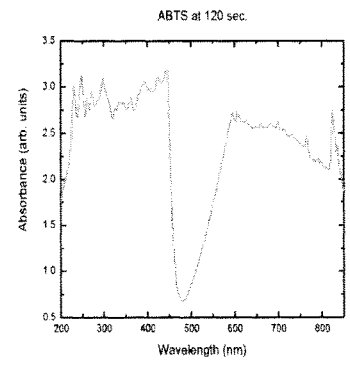
FIG. 13C is a diagram illustrating experimental data of optical measurement of glucose (analyte) using ABTS as a reagent according to an embodiment of the present invention.

FIGS. 13A-C are diagrams of experimental data (for glucose as a target analyte) that compares absorbance/transmittance spectrum measured with different reagents. As shown in FIGS. 13A-C, even for the same analyte, glucose in this case, the spectrum responses are different from different reagents. Detecting at the most sensitive wavelength can improve detection sensitivity and accuracy. Multicolor detection can be achieved by either using a multiple wavelength/color light source with a simple photodiode type detector, or a board spectrum light source with a spectrometer or color filter for detector. The reagents used are Potassium Iodine (KI), 3,3',5,5'-Tetramethylbenzidine (TMB), and 2,2'-azino-bis(3-ethylbenzothiazoline-6-sulphonic acid) (ABTS) in FIG. 13A, FIG. 13B, and FIG. 13C, respectively.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A method, comprising:

introducing at least one reagent into a fluid sample flowing through a conduit using at least one reagent dispenser located at an introduction point along the conduit;

making first optical measurements of an intensity of light $I_1$ passing through the fluid sample at time $t_1$ using at least one first detector located at a first detection point along the conduit downstream from the introduction point;

making second optical measurements of an intensity of light $I_2$ passing through the fluid sample at time $t_2$ using at least one second detector located at a second detection point along the conduit downstream from the first detection point; and comparing the first optical measurements with the second optical measurements to determine an amount of reaction, if any, the at least one reagent has had with target analyte in the fluid sample between the first detection point and the second detection point, wherein the comparing further comprises: determining a rate of change as $(I_2/I_{o2} - I_1/I_{o1})/(t_2 - t_1)$, wherein $I_{o1}$ is a baseline intensity reading taken of clean water using the at least one first detector located at the first detection point, and wherein $I_{o2}$ is another baseline intensity reading taken of the clean water using the at least one second detector located at the second detection point.

2. The method of claim 1, further comprising:

calibrating the at least one first detector and the at least one second detector in clean water.

3. The method of claim 1, further comprising:

determining a time delay $(t_2 - t_1)$ between the first detection point and the second detection point.

4. The method of claim 1, wherein a slug of the at least one reagent is introduced into the fluid sample with a concentration of the at least one reagent at a front and a back of the slug being less than the concentration of the at least one reagent at a center of the slug.

* * * * *